United States Patent [19]

Lange et al.

[11] Patent Number: 4,599,356
[45] Date of Patent: Jul. 8, 1986

[54] N-BENZOYL-N'-PHENYLUREAS AND THEIR USE FOR INSECT CONTROL

[75] Inventors: Arno Lange, Mannheim; Karl Kiehs, Lampertheim; Heinrich Adolphi, Limburgerhof, all of Fed. Rep. of Germany

[73] Assignee: BASF Aktiengesellschaft, Fed. Rep. of Germany

[21] Appl. No.: 555,393

[22] Filed: Nov. 28, 1983

Related U.S. Application Data

[63] Continuation of Ser. No. 337,284, Jan. 5, 1982, abandoned.

[30] Foreign Application Priority Data

Jan. 14, 1981 [DE] Fed. Rep. of Germany ....... 3100911

[51] Int. Cl.$^4$ ............... A01N 37/10; C07C 101/68
[52] U.S. Cl. ................................. 514/535; 560/34
[58] Field of Search ............ 560/34; 424/309; 514/535

[56] References Cited

U.S. PATENT DOCUMENTS 3,748,356  7/1973  Wellinga et al. ............ 560/34 X
4,234,600  11/1980  Sirrenberg et al. ........... 560/34 X Primary Examiner—Bernard Helfin
Attorney, Agent, or Firm—Keil & Weinkauf

[57] ABSTRACT

N-Benzoyl-N'-phenylureas of the formula

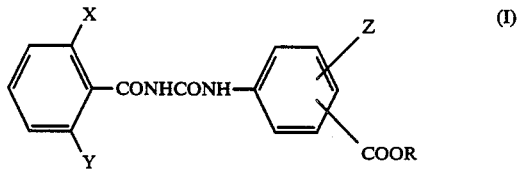

where X, Y, Z and R have the meanings given in the description, are used for insect control.

5 Claims, No Drawings

N-BENZOYL-N'-PHENYLUREAS AND THEIR USE FOR INSECT CONTROL

This is a continuation of application Ser. No. 337,284, filed Jan. 5, 1982 and now abandoned.

The present invention relates to N-benzoyl-N'-phenylureas, insecticides containing these compounds as active ingredients and a method of controlling insects with these active ingredients.

German Laid-Open Application DOS No. 2,843,851 discloses that N-benzoyl-N'-phenylureas are insecticidally active.

We have now found that N-benzoyl-N'-phenylureas of the formula

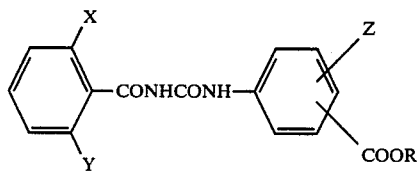
(I)

where X is chlorine, fluorine or methyl, Y is chlorine, fluorine or hydrogen, Z is bromine, chlorine, fluorine or hydrogen and R is primary or secondary alkyl of 3 to 12 carbon atoms, unsubstituted or alkyl-substituted cycloalkyl of 5 to 12 carbon atoms or adamantanyl, have a very powerful insecticidal action which is superior to that of conventional benzoylureas of a similar structure.

An alkyl radical R in formula I can be primary or secondary alkyl of 3 to 12 carbon atoms, such as isopropyl, sec.-butyl, pent-3-yl, 2,4-dimethyl-pent-3-yl, n-heptyl, 2,6-dimethyl-hept-4-yl, 2,2,4,4-tetramethyl-pent-3-yl, 1-methyl-7-ethyl-non-4-yl, 2,8-dimethyl-non-8-yl or 3,5,5-trimethyl-hex-1-yl. Suitable cycloalkyl radicals which have 5 to 12 carbon atoms and can be substituted by alkyl, especially alkyl of 1 to 4 carbon atoms, are, for example, cyclopentyl, cyclohexyl and 4-tert.-butylcyclohexyl.

Preferred N-benzoyl-N'-phenylureas are compounds of the formula I where X is fluorine or chlorine and Y is fluorine or hydrogen, and —COOR is in the p-position. R is preferably secondary alkyl of 4 to 9 carbon atoms.

The N-benzoyl-N'-phenylureas of the formula I are obtained by reacting a benzoyl isocyanate of the formula

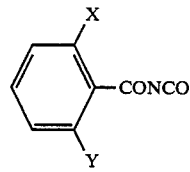
(II)

where X and Y have the above meanings, with an aminobenzoic acid ester of the formula

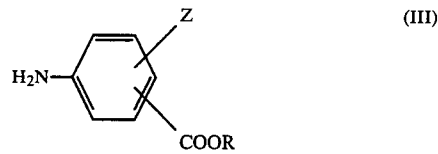
(III)

where Z and R have the above meanings, in the presence of an inert organic solvent at from 0° to 80° C.

The process for the preparation of the compounds according to the invention is carried out in the presence of a suitable solvent or diluent. Virtually all the inert organic solvents can be used, in particular aliphatic and aromatic hydrocarbons, which may be chlorinated or nitrated, such as benzene, toluene, the xylenes, the chlorobenzenes, gasoline, carbon tetrachloride, 1,2-dichloroethane, methylene chloride, chloroform and nitromethane; cyclic and acyclic ethers, such as diethyl ether, dibutyl ether, tetrahydrofuran and dioxane; acyclic and cyclic ketones, such as acetone, methyl ethyl ketone, methyl isopropyl ketone and cyclohexanone; and nitriles, such as acetonitrile and benzonitrile. Mixtures of these solvents can also be used.

The reaction temperature can be varied within a substantial range, in general from 0° to 80° C. Because it is exothermic, the reaction usually proceeds at from 20° to 60° C.

The reaction can generally be carried out under atmospheric pressure, either batchwise or continuously.

The reactants are preferably employed in the process in an equimolar ratio. An excess of one or other of the components provides no substantial advantages. The reaction proceeds virtually quantitatively.

The ureas of the formula I are obtained as solid products which are as a rule analytically pure, but may otherwise be purified by recrystallization. They are characterized by elementary analysis and melting point determination.

Advantageously, the substituted aminobenzoic acid ester of the formula III and the solvent or diluent are initially introduced into the reaction vessel and the isocyanate of the formula II is then added. After a reaction time of several hours, usually of 2 hours, the product is filtered off with suction and dried under reduced pressure.

Methods for preparing the benzoyl isocyanates of the formula II and the aminobenzoic acid esters of the formula III have been disclosed (J. Org. Chem. 28 (1963), 1805–1811; Organicum, 9th edition, 1969, pages 446 and 576, VEB Deutscher Verlag der Wissenschaften).

The ureas of the formula I can also be prepared by reacting an amide of the formula

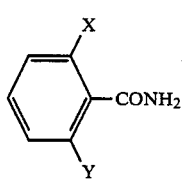
(IV)

with an isocyanate of the formula

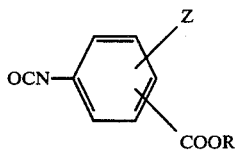

where X, Y, Z and R have the above meanings.

The reactants are used in equimolar amounts, in the presence or absence of an inert organic solvent. The reaction temperature is from 0° to 140° C., preferably from 60° to 100° C., and a catalyst, such as triethylamine, may be added. The same solvents as can be used in the reaction of compounds of the formula II with those of the formula III may be employed.

PREPARATION EXAMPLE 6.75 g of 2,4-dimethylpent-3-yl 4-amino-2-chlorobenzoate were dissolved in 80 ml of absolute toluene, and 4.6 g of 2,6-difluorobenzoyl isocyanate were added dropwise. The mixture was kept at 50° C. for 2 hours and was then filtered with suction at 0° C. The material on the filter was then dried at 40° C. in a drying cabinet under reduced pressure. 8.1 g of N-(2,6-difluorobenzoyl)-N'-[3-chloro-(2,4-dimethyl-pent-3-oxycarbonyl)-phenyl]-urea were obtained (Compound No. 1). Melting point: 135°–140° C.

The following compounds can be prepared, for example, by one of the processes described above:

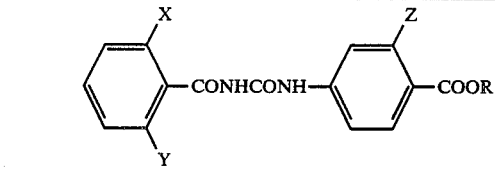

| No. | X   | Y   | Z   | R                        | m.p. [°C.]         |
|-----|-----|-----|-----|--------------------------|--------------------|
| 2   | Cl  | H   | Cl  | 2,4-Dimethyl-pentyl-(3)  | 152–154            |
| 3   | F   | F   | Cl  | 3,5,5-Trimethyl-n-hexyl  | 114–115            |
| 4   | Cl  | Cl  | Cl  | "                        | 185–186            |
| 5   | Cl  | H   | Cl  | "                        | 125–126            |
| 6   | CH3 | H   | Cl  | "                        | 148–150            |
| 7   | F   | F   | Cl  | n-Heptyl                 | 100–108            |
| 8   | Cl  | Cl  | Cl  | "                        | 125–127            |
| 9   | Cl  | H   | Cl  | "                        | 126–128            |
| 10  | CH3 | H   | Cl  | "                        | 133–135            |
| 11  | F   | F   | Cl  | 2,6-Dimethyl-heptyl-(4)  | 140–142            |
| 12  | Cl  | Cl  | Cl  | "                        | 145–147            |
| 13  | Cl  | H   | Cl  | "                        | 144–146            |
| 14  | CH3 | H   | Cl  | "                        | 104–106            |
| 15  | F   | F   | Cl  | Pentyl-(3)               | 150–152            |
| 16  | Cl  | Cl  | Cl  | "                        | 160–165            |
| 17  | Cl  | H   | Cl  | "                        | 149–150            |
| 18  | F   | F   | Cl  | 1-Methyl-7-ethyl-nonyl-(4)| 97–99             |
| 19  | Cl  | Cl  | Cl  | "                        | oil (n$_D^{25}$ = 1.5541) |
| 20  | Cl  | H   | Cl  | "                        | 90–95              |
| 21  | CH3 | H   | Cl  | "                        | 50–53              |
| 22  | F   | F   | Cl  | Adamantanyl              | 237–242            |
| 23  | Cl  | Cl  | Cl  | "                        | 232–234            |
| 24  | Cl  | H   | Cl  | "                        | 234–240            |
| 25  | F   | F   | Br  | 2,4-Dimethyl-pentyl-(3)  | 149–151            |
| 26  | F   | F   | H   | 2,6-Dimethyl-heptyl-(4)  | 154–156            |
| 27  | Cl  | Cl  | H   | "                        | 167–169            |
| 28  | F   | F   | Cl  | 4-tert.-Butyl-cyclohexyl | 217–220            |
| 29  | F   | H   | Cl  | "                        | 217–220            |
| 30  | Cl  | H   | H   | 2,6-Dimethyl-heptyl-(4)  |                    |
| 31  | F   | F   | H   | 2,4-Dimethyl-pentyl-(3)  | 155–159            |
| 32  | F   | Cl  | H   | "                        |                    |
| 33  | Cl  | Cl  | H   | "                        | 172–177            |
| 34  | Cl  | H   | H   | "                        | 163–165            |
| 35  | F   | F   | Cl  | 2,2,4,4-Tetramethyl-pentyl-(3) |              |
| 36  | Cl  | Cl  | Cl  | 2,2,4,4-Tetramethyl-pentyl-(3) |              |
| 37  | Cl  | H   | Cl  | 2,2,4,4-Tetramethyl-pentyl-(3) |              |
| 38  | F   | F   | F   | 2,4-Dimethyl-pentyl-(3)  |                    |
| 39  | Cl  | Cl  | F   | "                        |                    |
| 40  | Cl  | H   | F   | "                        |                    |
| 41  | F   | F   | F   | 2,6-Dimethyl-heptyl-(4)  |                    |
| 42  | Cl  | Cl  | F   | "                        |                    |
| 43  | Cl  | H   | F   | "                        |                    |
| 44  | F   | F   | Cl  | sec.-Butyl               | 168–172            |
| 45  | Cl  | Cl  | Cl  | "                        | 165–169            |
| 46  | Cl  | H   | Cl  | "                        | 155–157            |
| 47  | F   | F   | Cl  | Isopropyl                |                    |
| 48  | Cl  | Cl  | Cl  | "                        |                    |
| 49  | Cl  | H   | Cl  | "                        |                    |
| 50  | F   | F   | F   | Pentyl-(3)               |                    |
| 51  | Cl  | Cl  | F   | "                        |                    |
| 52  | Cl  | H   | F   | "                        |                    |

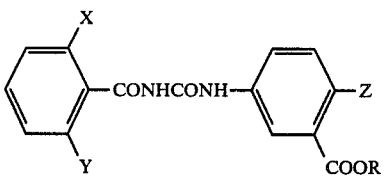

| No. | X   | Y   | Z   | R                         | m.p. [°C.] |
|-----|-----|-----|-----|---------------------------|------------|
| 53  | F   | F   | Cl  | 2,4-Dimethyl-pentyl-(3)   | 172–174    |
| 54  | Cl  | Cl  | Cl  | "                         | 155–158    |
| 55  | Cl  | H   | Cl  | "                         | 195–198    |
| 56  | F   | F   | Cl  | 2,6-Dimethyl-n-heptyl-(4) | 180–182    |
| 57  | Cl  | Cl  | Cl  | "                         | 178–181    |
| 58  | Cl  | H   | Cl  | "                         | 146–150    |
| 59  | F   | F   | Cl  | 2,8-Dimethyl-nonyl-(5)    | 130–134    |
| 60  | Cl  | Cl  | Cl  | "                         | 100–104    |
| 61  | Cl  | H   | Cl  | "                         | 110–112    |

The N-benzoyl-N'-phenylureas of the formula I according to the invention are suitable for effectively combating pests from the classes of insects, arachnids and nematodes. They may be employed as pesticides for protecting crops, and in the hygiene, stores protection and veterinary sectors.

Examples of injurious insects from the Lepidoptera order are *Plutella maculipennis, Leucoptera coffeella, Hyponomeuta malinellus, Argyresthia conjugella, Sitotroga cerealella, Phthorimaea operculella, Capua reticulana, Sparganothis pilleriana, Cacoecia murinana, Tortrix viridana, Clysia ambiguella, Evetria buoliana, Polychrosis botrana, Cydia pomonella, Laspeyresia molesta, Laspeyresia funebrana, Ostrinia nubilalis, Loxostege sticticalis, Ephestia kuehniella, Chilo suppressalis, Galleria mellonella, Malacosoma neustria, Dendrolimus pini, Thaumatopoea pityocampa, Phalera bucephala, Cheimatobia brumata, Hibernia defoliaria, Bupalus piniarus, Hyphantria cunea, Agrotis segetum, Agrotis ypsilon, Barathra brassicae, Cirphis unipuncta, Prodenia litura, Laphygma exigua, Panolis flammea, Earias insulana, Plusia gamma, Alabama argillacea, Lymantria dispar., Lymantria monocha, Pieris brassicae,* and *Aporia crataegi;* examples from the Coleoptera order are *Blitophaga undata, Melanotus communis, Limonius californicus, Agriotes lineatus, Agricotes obscurus, Agrilus sinuatus, Meligethes aeneus, Atomaria linearis, Epilachna varives-*

*tris, Phyllopertha horticola, Popillia japonica, Melolontha melolontha, Melolontha hippocastani, Amphimallus solstitialis, Crioceris asparagi, Lema melanopus, Leptinotarsa decemlineata, Phaedon cochleariae, Phyllotreta nemorum, Chaetocnema tibialis, Phylloides chrysocephala, Diabrotica 12-punctata, Cassida nebulosa, Bruchus lentis, Bruchus rufimanus, Bruchus pisorum, Sitona lineatus, Otiorrhynchus sulcatus, Otiorrhynchus ovatus, Hylobies abietis, Byctiscus betulae, Anthonomus pomorum, Anthonomus grandis, Ceuthorrhynchus assimilis, Ceuthorrhynchus napi, Sitophilus granaria, Anisandrus dispar, Ips typographus,* and *Blastophagus piniperda;* examples from the Diptera order are *Lycoria pectoralis, Mayetiola destructor, Dasyneura brassicae, Contarinia tritici, Haplodiplosis equestris, Tipula paludosa, Tipula oleracea, Dacus cucurbitae, Dacus oleae, Ceratitis capitata, Rhagoletis cerasi, Rhagoletis pomonella, Anastrepha ludens, Oscinella frit, Phorbia coarctata, Phorbia antiqua, Phorbia brassicae, Pegomya hyoscyami, Anopheles maculipennis, Culex pipiens, Aedes aegypti, Aedes vexans, Tabanus bovinus, Tipula paludosa, Musca domestica, Fannia canicularis, Muscina stabulans, Glossina morsitans, Oestrus ocis, Chrysomya macellaria, Chrysomya hominivorax, Lucilia cuprina, Lucilia sercata,* and *Hypoderma lineata;* examples from the Hymenoptera order are *Athalia rosae, Haplocampa minuta, Monomorium pharaonis, Solenopsis geminata,* and *Atta sexdens;* examples from the Heteroptera order are *Nezara viridula, Eurygaster integriceps, Blissus leucopterus, Dysdercus cingulatus, Dysdercus intermedius, Piesma quadrata,* and *Lygus pratensis;* examples from the Homoptera order are *Perkinsiella saccharicida, Nilaparvata lugens, Empoasca fabae, Psylla mali, Psylla piri, Trialeurodes vaporariorum, Aphis fabae, Aphis pomi, Aphis sambuci, Aphidula nasturtii, Cerosipha gossypii, Sappaphis mali, Sappaphis mala, Dysphis radicola, Brachycaudus cardui, Brevicoryne brassicae, Phorodon humuli, Rhopalomyzus ascalonicus, Myzodes persicae, Myzus cerasi, Dysaulacorthum pseudosolani, Acyrthosiphon onobrychis, Macrosiphon rosae, Megoura viciae, Schizoneura lanuginosa, Pemphigus bursarius, Dreyfusia nordmannianae, Dreyfusia piceae, Adelges laricis,* and *Viteus vitifolii;* examples from the Isoptera order are *Reticulitermes lucifugus, Calotermes flavicollis, Leucotermes flavipes,* and *Termes natalensis;* examples from the Orthoptera order are *Forficula auricularia, Acheta domestica, Gryllotalpa gryllotalpa, Tachycines asynamorus, Locusta migratoria, Stauronotus maroccanus, Schistocerca peregrina, Nomadacris septemfasciata, Melanoplus spretus, Melanoplus femur-rubrum, Blatta orientalis, Blatella germanica, Periplaneta americana,* and *Blabera gigantea.*

The active ingredients may be applied as such, in the form of formulations, or of ready-to-use application forms prepared therefrom, e.g., directly sprayable solutions, powders, suspensions, dispersions, emulsions, oil dispersions, pastes, dusts, broadcasting agents, or granules by spraying, atomizing, dusting, broadcasting or watering. The forms of application depend entirely on the purpose for which the agents are being used; in any case they should ensure as fine a distribution of the active ingredient as possible.

For the preparation of solutions, emulsions, pastes and oil dispersions to be sprayed direct, mineral oil fractions of medium to high boiling point, such as kerosene or diesel oil, further coal-tar oils, and oils of vegetable or animal origin, aliphatic, cyclic and aromatic hydrocarbons such as benzene, toluene, xylene, paraffin, tetrahydronaphthalene, alkylated naphthalenes and their derivatives such as methanol, ethanol, propanol, butanol, chloroform, carbon tetrachloride, cyclohexanol, cyclohexanone, chlorobenzene, isophorone, and strongly polar solvents such as dimethylformamide, dimethylsulfoxide, N-methylpyrrolidone, and water are suitable.

Aqueous formulations may be prepared from emulsion concentrates, pastes, oil dispersions or wettable powders by adding water. To prepare emulsions, pastes and oil dispersions the ingredients as such or dissolved in an oil or solvent may be homogenized in water by means of wetting or dispersing agents, adherents or emulsifiers. Concentrates which are suitable for dilution with water may be prepared from active ingredient, wetting agent, adherent, emulsifying or dispersing agent and possibly solvent or oil.

Examples of surfactants are: alkali metal, alkaline earth metal and ammonium salts of ligninsulfonic acid, naphthalene-sulfonic acids, phenolsulfonic acids, alkylaryl sulfonates, alkyl sulfates, and alkyl sulfonates, alkali metal and alkaline earth metal salts of dibutylnaphthalenesulfonic acid, lauryl ether sulfate, fatty alcohol sulfates, alkali metal and alkaline earth metal salts of fatty acids, salts of sulfated hexadecanols, heptadecanols, and octadecanols, salts of sulfated fatty alcohol glycol ethers, condensation products of sulfonated naphthalene and naphthalene derivatives with formaldehyde, condensation products of naphthalene or naphthalenesulfonic acids with phenol and formaldehyde, polyoxyethylene octylphenol ethers, ethoxylated isooctylphenol, ethoxylated octylphenol and ethoxylated nonylphenol, alkylphenol polyglycol ethers, tributylphenyl polyglycol ethers, alkylaryl polyester alcohols, isotridecyl alcohol, fatty alcohol ethylene oxide condensates, ethoxylated castor oil, polyoxyethylene alkyl ethers, ethoxylated polyoxypropylene, lauryl alcohol polyglycol ether acetal, sorbitol esters, lignin, sulfite waste liquors and methyl cellulose.

Powders, dusts and broadcasting agents may be prepared by mixing or grinding the active ingredients with a solid carrier.

Granules, e.g., coated, impregnated or homogeneous granules, may be prepared by bonding the active ingredients to solid carriers. Examples of solid carriers are mineral earths such as silicic acid, silica gels, silicates, talc, kaolin, Attaclay, limestone, lime, chalk, bole, loess, clay, dolomite, diatomaceous earth, calcium sulfate, magnesium sulfate, magnesium oxide, ground plastics, fertilizers such as ammonium sulfate, ammonium phosphate, ammonium nitrate, and ureas, and vegetable products such as grain flours, bark meal, wood meal, and nutshell meal, cellulosic powders, etc.

The formulations generally contain from 0.1 to 95, and preferably 0.5 to 90, % by weight of active ingredient.

The amount of active ingredient in the ready-to-use formulations may vary within a wide range; it is generally from 0.0001 to 10%, preferably from 0.01 to 1%.

Examples of formulations are given below.

I. 5 parts by weight of compound no. 14 was intimately mixed with 95 parts by weight of particulate kaolin. A dust was obtained containing 5% by weight of the active ingredient.

II. 30 parts by weight of compound no. 15 was intimately mixed with a mixture consisting of 92 parts by weight of powdered silica gel and 8 parts by weight of paraffin oil which had been sprayed onto the surface of this silica gel. A formulation of the active ingredient was obtained having good adherence.

III. 10 parts by weight of compound no. 23 was dissolved in a mixture consisting of 90 parts by weight of xylene, 6 parts by weight of the adduct of 8 to 10 moles of ethylene oxide with 1 mole of oleic acid-N-monoethanolamide, 2 parts by weight of the calcium salt of dodecylbenzenesulfonic acid, and 2 parts by weight of the adduct of 40 moles of ethylene oxide with 1 mole of castor oil.

IV. 20 parts by weight of compound no. 24 was dissolved in a mixture consisting of 60 parts by weight of cyclohexanone, 30 parts by weight of isobutanol, 5 parts by weight of the adduct of 7 moles of ethylene oxide with 1 mole of isooctylphenol, and 5 parts by weight of the adduct of 40 moles of ethylene oxide with 1 mole of castor oil.

V. 80 parts by weight of compound no. 52 was well mixed with 3 parts by weight of the sodium salt of diisobutylnaphthalene-α-sulfonic acid, 10 parts by weight of the sodium salt of a lignin-sulfonic acid obtained from a sulfite waste liquor, and 7 parts by weight of powdered silica gel, and triturated in a hammer mill.

The active ingredients may also be successfully used in the ultra-low volume method, where it is possible to apply formulations containing more than 95 wt% of active ingredient, or even the 100% active ingredient.

When the active ingredient are applied in the open, the rates are from 0.2 to 10, preferably 0.5 to 2.0, kg/ha.

There may be added to the active ingredients (if desired, immediately before use (tankmix)) oils of various types, herbicides, fungicides, other insecticides and bactericides. These agents may be added to the active ingredients according to the invention in a weight ratio of from 1:10 to 10:1.

Examples of active ingredients which may be admixed are as follows:

1,2-dibromo-3-chloropropane, 1,3-dichloropropene, 1,3-dichloropropene+1,2-dichloropropane, 1,2-dibromoethane, 2-sec-butylphenyl-N-methylcarbamate, o-chlorophenyl-N-methylcarbamate, 3-isopropyl-5-methylphenyl-N-methylcarbamate, o-isopropoxyphenyl-N-methylcarbamate, 3,5-dimethyl-4-methylmercaptophenyl-N-methylcarbamate, 4-dimethylamino-3,5-xylyl-N-methylcarbamate, 2-(1,3-dioxolan-2-yl)-phenyl-N-methylcarbamate, 1-naphthyl-N-methylcarbamate, 2,3-dihydro-2,2-dimethylbenzofuran-7-yl-N-methylcarbamate, 2,2-dimethyl-1,3-benzodioxol-4-yl-N-methylcarbamate, 2-dimethylamino-5,6-dimethyl-4-pyrimidinyldimethylcarbamate, 2-methyl-2-(methylthio)-propionaldehyde-O-(methylcarbamoyl)-oxime, S-methyl-N-[(methyl)carbamoyl)-oxy]-thioacetimidate, methyl-N',N'-dimethyl-N-[(methylcarbamoyl)-oxy]-1-thiooxamidate, N-(2-methyl-4-chlorophenyl)-N'N'-dimethylformamidine, tetrachlorothiophene, 1-(2,6-difluorobenzyl)-3-(4-chlorophenyl)-urea, O,O-dimethyl-O-(p-nitrophenyl)-phosphorothioate, O,O-diethyl-O-(p-nitrophenyl)-phosphorothioate, O-ethyl-O-(p-nitrophenyl)-phenylphosphonothioate, O,O-dimethyl-O-(3-methyl-4-nitrophenyl)-phosphorothioate, O,O-diethyl-O-(2,4-dichlorophenyl)-phosphorothioate, O-ethyl-O-(2,4-dichlorophenyl)-phenylphosphonothioate, O,O-dimethyl-O-(2,4,5-trichlorophenyl)-phosphorothioate, O-ethyl-O-(2,4,5-trichlorophenyl)-ethyl-phosphonothioate, O,O-dimethyl-O-(4-bromo-2,5-dichlorophenyl)-phosphorothioate, O,O-dimethyl-O-(2,5-dichloro-4-iodophenyl)-phosphorothioate, O,O-dimethyl-O-(3-methyl-4-methylthiophenyl)-phosphorothioate, O-ethyl-O-(3-methyl-4-methylthiophenyl)-isopropylphosphoramidate, O,O-diethyl-O-[p-(methylsulfynyl)-phenyl]-phosphorothioate, O-ethyl-S-phenylethyl-phosphonodithioate, O,O-diethyl-[2-chloro-1-(2,4-dichlorophenyl)-vinyl]-phosphate, O,O-dimethyl-[-2-chloro-1-(2,4,5-trichlorophenyl)]-vinylphosphate, O,O-dimethyl-S-(1-phenyl)-ethylacetate phosphorodithioate, bis-(dimethylamino)-fluorophosphine oxide, octamethyl-pyrophosphoramide, O,O,O,O-tetraethyldithiopyrophosphate, S-chloromethyl-O,O-diethyl-phosphorodithioate, O-ethyl-S,S-dipropyl-phosphorodithioate, O,O-dimethyl-O-2,2-dichlorovinylphosphate, O,O-dimethyl-1,2-dibromo-2,2-dichloroethylphosphate, O,O-dimethyl-2,2,2-trichloro-1-hydroxyethylphosphonate, O,O-dimethyl-S-[1,2-biscarbethoxyethyl-(1)]-phosphorodithioate, O,O-dimethyl-O-(1-methyl-2-carbomethoxyvinyl)-phosphate, O,O-dimethyl-S-(N-methylcarbamoylmethyl)-phosphorodithioate, O,O-dimethyl-S-(N-methylcarbamoylmethyl)-phosphorothioate, O,O-dimethyl-S-(N-methoxyethylcarbamoylmethyl)-phosphorodithioate, O,O-dimethyl-S-(N-formyl-N-methylcarbamoylmethyl)-phosphorodithioate, O,O-dimethyl-O-[1-methyl-2-(methylcarbamoyl)-vinyl]-phosphate, O,O-dimethyl-O-[(1-methyl-2-dimethylcarbamoyl)-vinyl]-phosphate, O,O-dimethyl-O-[(1-methyl-2-chloro-2-diethylcarbamoyl)-vinyl]-phosphate, O,O-diethyl-S-(ethylthiomethyl)-phosphorodithioate, O,O-diethyl-S-[(p-chlorophenylthio)-methyl]-phosphorodithioate, O,O-dimethyl-S-(2-ethylthioethyl)-phosphorothioate, O,O-dimethyl-S-(2-ethylthioethyl)-phosphorodithioate, O,O-dimethylsulfynylethyl)-phosphorothioate, O,O-diethyl-S-(2-ethylthioethyl)-phosphorodithioate, O,O-diethyl-S-(2-ethylsulfynylethyl)-phosphorothioate, O,O-diethylthiophosphoryliminophenyl-acetonitrile, O,O-diethyl-S-(2-chloro-1-phthalimidoethyl)-phosphorodithioate, O,O-diethyl-S-[6-chlorobenzoxazolon-(2)-yl-(3)]-methyldithiophosphate, O,O-dimethyl-S-[2-methoxy-1,3,4-thiadiazol-5-onyl-(4)-methyl]-phosphorodithioate, O,O-diethyl-O-[3,5,6-trichloropyridyl-(2)]-phosphorothioate, O,O-diethylO-(2-pyrazinyl)-phosphorothioate, O,O-diethyl-O-[2-isopropyl-4-methylpyrimidinyl-(6)]-phosphorothioate, O,O-diethyl-O-[2-(diethylamino)-6-methyl-4-pyrimidinyl]-thionophosphate, O,O-dimethyl-S-(4-oxo-1,2,3-benzotriazin-3-[4H]-yl-methyl)-phosphorodithioate, O,O-dimethyl-S-[(4,6-diamino-1,3,5-triazin-2-yl)-methyl]-phosphorodithioate, O,O-diethyl-(1-phenyl-1,2,4-triazol-3-yl)-thionophosphate, O,S-dimethylphosphoroamidothioate, O,S-dimethyl-N-acetylphosphoramidothioate, γ-hexachlorocyclohexane, 1,1-di-(p-methoxyphenyl)-2,2,2-trichloroethane, 6,7,8,9,10,10-hexachloro-1,5,5a,6,9,9a-hexahydro-6,9-methano-2,4,3-benzodioxathiepine-3-oxide, pyrethrins, DL-2-allyl-3-methyl-cyclopenten-(2)-on-(1)-yl-(4)-DL-cis,trans-chrysanthemate, 5-benzylfuryl-(3)-methyl-DL-cis,trans-chrysanthemate, 3-phenoxybenzyl(±)-cis,trans-2,2-dimethyl-3-(2,2-dichlorovinyl)-cyclopropanecarboxylate, α-cyano-3-phenoxybenzyl(±)-cis,trans-2,2-dimethyl-3-(2,2-dichlorovinyl)-cyclopropane carboxylate, (s)-α-cyano-3-phenoxybenzyl-cis(1R,3R)-2,2-dimethyl-3-(2,2-dibromovinyl)-cyclopropane carboxylate, 3,4,5,6-tetrahydrophthalimidoethyl-DL-cis,trans-chrysanthemate, 2-methyl-5-(2-propynyl)-3-furylmethyl-chrysanthemate, and α-cyano-3-phenoxybenzyl- -isopropyl-4-chlorophenylacetate.

The following examples illustrate the biological action of the novel compounds. The prior art active ingredients used for comparison purposes were N-(2,6-difluorobenzoyl)-N'-(3-chloro-4-tert-butoxyphenyl)-urea, N-(2-chlorobenzoyl)-N'-(3-chloro-4-tert-butoxycarbonylphenyl)-urea and N-(2-methylbenzoyl)-N'-(3-chloro-4-tert-butoxycarbonylphenyl)-urea (German Laid-Open Application No. 2,843,852).

The active ingredients are numbered as in the foregoing table.

EXAMPLE A

Breeding experiment with mosquito larvae (Aedes aegypti)

30 to 40 larvae of Aedes aegypti in the 4th larval stage were introduced into 200 ml of tapwater to which a formulation consisting of 10 wt% of active ingredient and 90 wt% of an emulsifier mixture consisting of 10% of ethoxylated castor oil, 20% of ethoxylated isooctyl phenol and 70% of cyclohexanone had been added.

The temperature at which the experiment was carried out was 25° C. Pupation and hatching of the adults were assessed, an untreated control being used for reference. During the 12 hours of the experiment, a conventional pulverized fish food was fed once.

In this test, active ingredients nos. 1, 2, 3, 5, 6, 9, 10, 13 and 16 had a better action than the comparative compounds.

EXAMPLE B

Breeding experiment with cotton stainers (Dysdercus intermedius)

50 g of cotton seed was swollen for 24 hours in aqueous formulations consisting of 10 wt% of active ingredient and 90 wt% of an emulsifier mixture consisting of 10% of ethoxylated castor oil, 20% of ethoxylated isooctyl phenol and 70% of cyclohexanone. The supernatant liquid was poured off.

20 cotton stainers in the penultimate larval stage were then placed in 1 liter jars, the bottoms of which were covered by moist sand. These animals were fed exclusively for 7 days on the pretreated seed. Subsequently, untreated food was then proffered.

It was observed whether the animals
(a) survived, and
(b) underwent ecdysis to give adults.

In this test, active ingredients nos. 1, 2, 3, 4, 5, 7, 8, 9, 10, 11, 12, 13, 14, 15 and 16 had a better action than the comparative agents.

We claim:
1. An N-benzoyl-N'-phenylurea of the formula

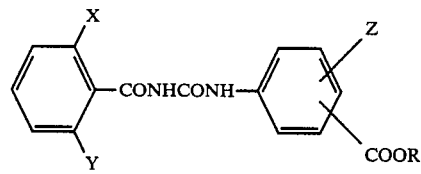

wherein X is chlorine or fluorine, Y is fluorine or hydrogen Z is chlorine or hydrogen and R is 2,4-dimethylpent-3-yl, 2,6-dimethylhept-4-yl or 2,2,4,4-tetramethylpent-3-yl.

2. An N-benzoyl-N'-phenylurea of the formula I as defined in claim 1, wherein Z is chlorine.

3. An N-benzoyl-N'-phenylurea of the formula I as defined in claim 1, wherein —COOR is in the p-position.

4. An insecticidal agent containing inert additives and from 0.5 to 90% by weight of an N-benzoyl N'-phenylurea of the formula I as defined in claim 1.

5. A process for combating insects, wherein an insecticidally effective amount of an N-benzoyl-N'-phenylurea of the formula I as claimed in claim 1 is allowed to act on the insects and/or their habitat.

* * * * *